(12) United States Patent
Lourdel et al.

(10) Patent No.: US 7,479,156 B2
(45) Date of Patent: Jan. 20, 2009

(54) VERTEBRAL ANCHORING DEVICE AND ITS BLOCKING DEVICE ON A POLYAXIAL SCREW

(75) Inventors: Rodolphe Lourdel, Beuvry (FR); Jean-Yves Leroy, Campagne les Hesdin (FR); Arnaud Pommier, Raimbeaucourt (FR); Pascal Rokegem, St Laurent Blangy (FR)

(73) Assignee: Choice Spine, LP, Knoxville, TN (US)

( * ) Notice: Subject to any disclaimer, the term of this patent is extended or adjusted under 35 U.S.C. 154(b) by 0 days.

(21) Appl. No.: 10/697,034

(22) Filed: Oct. 31, 2003

(65) Prior Publication Data
US 2004/0097933 A1    May 20, 2004

(30) Foreign Application Priority Data
Nov. 19, 2002    (FR)    .................................. 02 14454

(51) Int. Cl.
    *A61B 17/70*    (2006.01)
(52) U.S. Cl. ....................................... 606/266; 606/270
(58) Field of Classification Search ................. 606/61, 606/72, 73, 246, 250–262, 264–275, 278–279, 606/300–302, 305, 319
    See application file for complete search history.

(56) References Cited

U.S. PATENT DOCUMENTS

| 4,805,602 | A | * | 2/1989 | Puno et al. ..................... 606/61 |
|---|---|---|---|---|
| 5,360,431 | A | * | 11/1994 | Puno et al. ..................... 606/72 |
| 5,562,663 | A | | 10/1996 | Wisnewski et al. |
| 5,658,285 | A | * | 8/1997 | Marnay et al. ................. 606/61 |
| 5,672,176 | A | * | 9/1997 | Biedermann et al. .......... 606/61 |
| 5,690,630 | A | * | 11/1997 | Errico et al. ................... 606/61 |
| 5,882,350 | A | | 3/1999 | Ralph et al. |
| 5,998,539 | A | * | 12/1999 | Morishima et al. ........... 524/591 |
| 6,090,111 | A | * | 7/2000 | Nichols ........................ 606/61 |
| 6,641,586 | B2 | * | 11/2003 | Varieur ........................ 606/61 |
| 6,755,835 | B2 | * | 6/2004 | Schultheiss et al. ........... 606/73 |
| 7,211,086 | B2 | * | 5/2007 | Biedermann et al. .......... 606/61 |
| 2002/0111628 | A1 | * | 8/2002 | Ralph et al. ................... 606/61 |

(Continued)

FOREIGN PATENT DOCUMENTS

DE    100 05 386 A1    8/2001

(Continued)

*Primary Examiner*—Eduardo C Robert
*Assistant Examiner*—James L Swiger, III
(74) *Attorney, Agent, or Firm*—Luedeka, Neely & Graham, PC

(57) ABSTRACT

A vertebral anchoring device including a polyaxial anchoring screw having a spherical head; a connecting rod; a connection element for receiving portions of the connecting rod; a clip having a pressure screw positionable to engage the connecting rod; and a connector installable on the spherical head for receiving the connecting rod. The connector includes a socket and a ring which co-act with one other about the spherical head of the screw in an installed orientation. The socket includes two portions bridged together at an upper level of the socket so that the two portions are positionable in a spaced apart orientation to enable the socket to be installed on the spherical head. Pressure of the pressure screw against the connecting rod bears the connecting rod against the ring which bears the ring against the spherical head of the screw.

7 Claims, 3 Drawing Sheets

U.S. PATENT DOCUMENTS

2002/0123752 A1* 9/2002 Schultheiss et al. ........... 606/73
2003/0125741 A1* 7/2003 Biedermann et al. .......... 606/61
2005/0059972 A1* 3/2005 Biscup ........................ 606/73
2006/0025771 A1* 2/2006 Jackson ....................... 606/61

FOREIGN PATENT DOCUMENTS

FR 2 794 637 12/2000
WO 99/65415 12/1999

* cited by examiner

VERTEBRAL ANCHORING DEVICE AND ITS BLOCKING DEVICE ON A POLYAXIAL SCREW

The present invention relates to a vertebral anchoring device comprising on each connector a blocking device permitting, after angular adjustment of said connector, its securement on a polyaxial screw with a spherical head.

There is known from U.S. Pat. No. 2,346,346 of Apr. 11, 1944, an external osseous anchoring device comprising connectors interconnected by a connecting rod, whilst each connector is secured to a support or to the osseous body by means of an anchoring screw with a spherical head.

Each connector is constituted by a cylindrical sleeve comprising at each end a bore of a different diameter permitting respectively the emplacement of the screw through said sleeve and the retention of the spherical head within this latter.

Each connector comprises a blocking device permitting simultaneously the immobilization of the connecting rod within the sleeve and the securement of this latter about the spherical head of the screw.

It is to be noted that for each emplacement of this anchoring device, it is imperative to connect the anchoring screw and the connector together before securement of said screw with either a support or a corresponding bone.

In this case, the spherical head of the screw is located disposed within the connector, giving rise to a difficult use of this latter for its anchoring with the support or the bone.

The object of the present invention consists in providing a connector and its blocking device which are assembled and freely mounted in rotation on the spherical head of an anchoring screw in the factory, to form a pre-assembled assembly before its implantation in the bone of a vertebral body.

To this end, the connector and the blocking device of the vertebral anchoring device according to the present invention permit receiving any type of anchoring screw with a spherical head, even those having an external diameter of the osseous anchoring screw thread greater than that of said spherical head.

The vertebral anchoring device according to the present invention comprises a connector, a connecting rod and a polyaxial anchoring screw comprising a spherical head and a screw-threaded body whose external diameter d at the summit of the screw threads can be greater than the external diameter a of the spherical head, each connector being constituted by a connecting element comprising vertical branches delimiting an opening of U shape, and a locking clip provided with a pressure screw for blocking in the bottom of the U of the connecting rod, said connecting element being pierced at its middle with a vertical bore permitting receiving opposite the opening a blocking device formed by a ring and a screw-threaded socket for the emplacement and positioning of the connector on the spherical head of the anchoring screw.

The vertebral anchoring device according to the present invention comprises a connecting element whose central bore comprises, from the bottom of the U shaped opening, a first circular portion and a second screw-threaded portion whose internal diameter is greater than that of the first portion so as to define an internal shoulder.

The vertebral anchoring device according to the present invention comprises a connecting element whose internal diameter $d_1$ of the circular portion of the central bore is less than the external diameter d of the screw-threaded portion or a of the spherical head of the anchoring screw.

The vertebral anchoring device according to the present invention comprises a blocking device whose ring comprises a cylindrical smooth portion bordered at one of its ends by a small collar.

The vertebral anchoring device according to the present invention comprises a blocking device whose external diameter of the cylindrical portion of the ring is slightly less than the internal diameter $d_1$ of the circular portion of the central bore, whilst the external diameter of the small collar is greater than the internal diameter $d_1$.

The vertebral anchoring device according to the present invention comprises a blocking device whose socket is constituted by a cylindrical body having a screw-threaded external surface and an internally opening bore provided at one of its ends with a diametral reduction forming an internal bearing area which is a portion of a sphere.

The vertebral anchoring device according to the present invention comprises a blocking device whose socket comprises on its external surface and in prolongation of the screw-threaded portion, an unscrew-threaded shoulder, and opposite the shoulder, notches disposed at regular intervals about the periphery of said socket.

The vertebral anchoring device according to the present invention comprises a blocking device whose socket comprises, in a longitudinal direction, two opposed slots partially cutting the length of the cylindrical body into two separate and identical portions.

The vertebral anchoring device according to the present invention comprises a blocking device whose two separate portions of the socket are connected together at the level of the shoulder by a bridge defining on the one hand a maximum opening before a rupture of the slots at the level of the internal support surface of part spherical shape, and on the other hand a maximum elasticity of the socket.

The accompanying drawings, given by way of example, permit better understanding of the invention, the invention, its characteristics and the advantages which it is adapted to provide:

Figure 1:
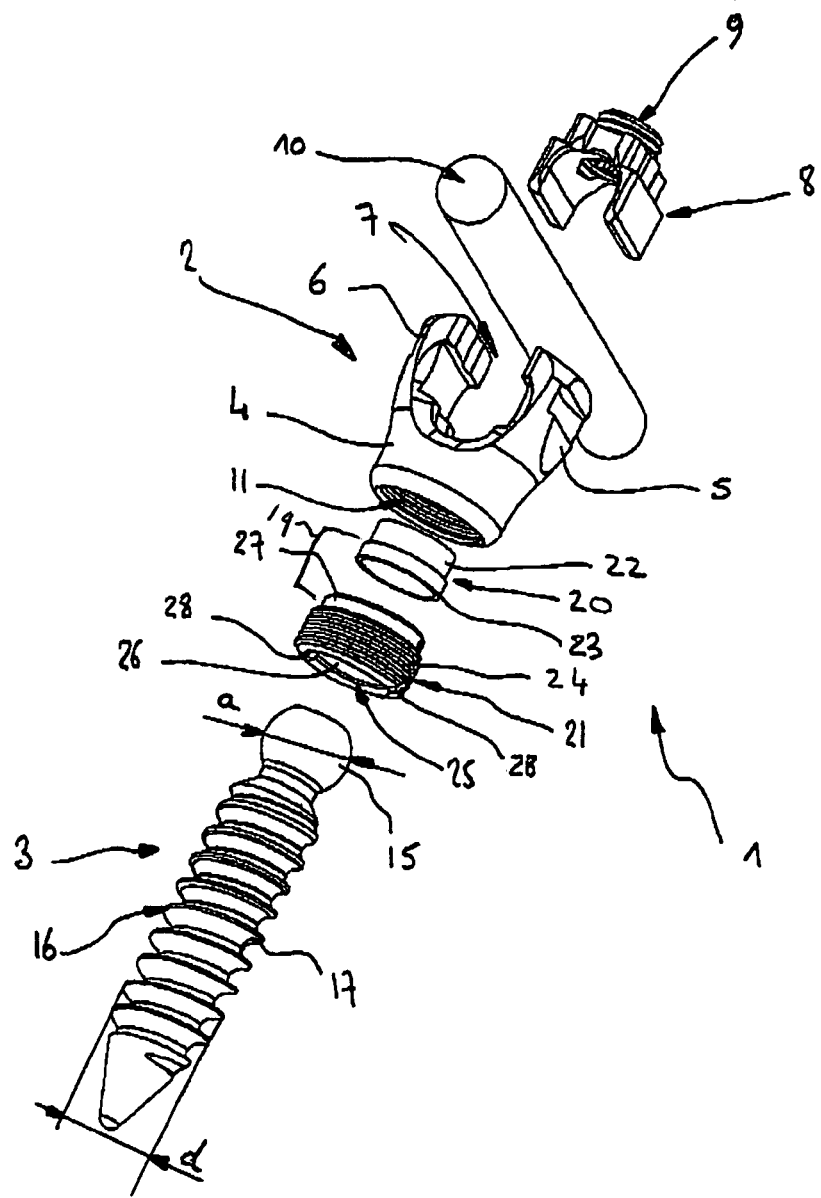
FIG. 1 is an exploded perspective view showing the vertebral anchoring device and its blocking device according to the present invention.
Figure 2:
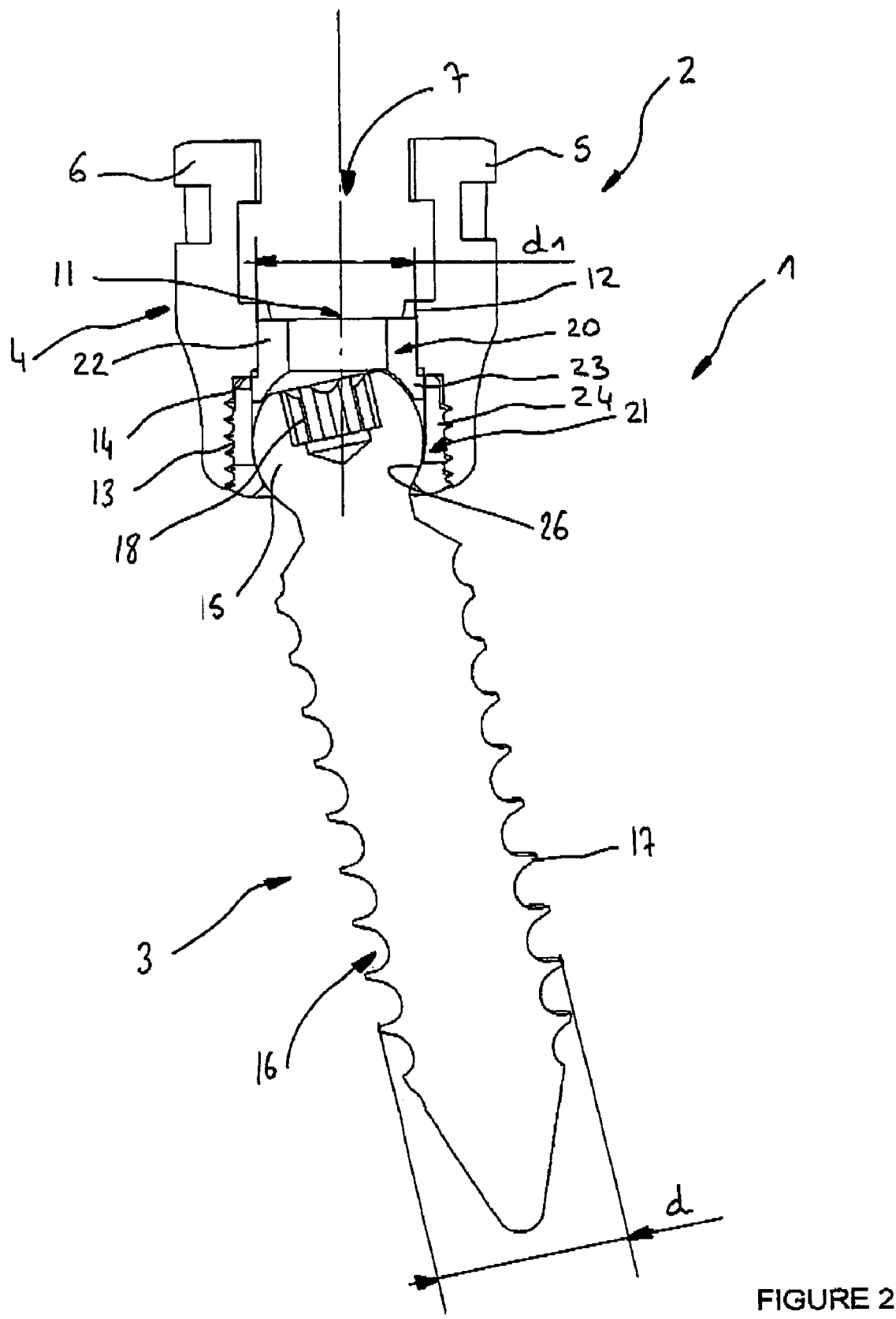
FIG. 2 is a cross-sectional view showing the vertebral anchoring device and its blocking device according to the present invention, in assembled position.
Figure 3:
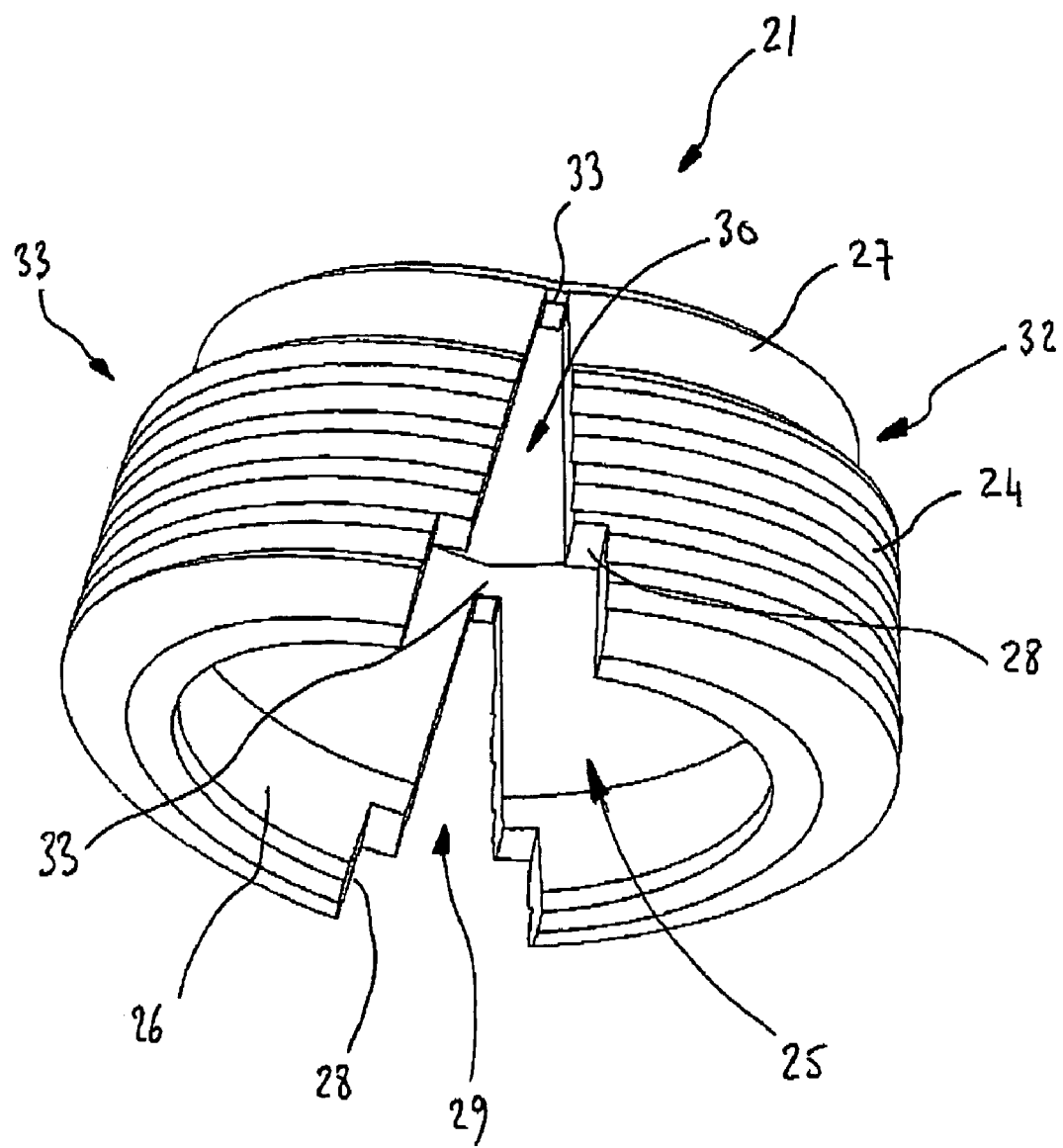
FIG. 3 is a perspective view showing the screw-threaded socket with elastic deformation of the blocking device according to the present invention.

There is shown in FIGS. 1 to 3 a vertebral anchoring device 1 comprising connectors 2 interconnected by connecting rods 10, whilst each connector is fixed in each vertebra of the rachidial segment to be corrected, by an anchoring screw 3.

Each connector 2 is constituted by a connection element 4 comprising vertical branches 5 and 6 delimiting an opening 7 of U shape, a clip 8 provided with a pressure screw 9 for blocking in the bottom of the U shape of the connection element 4 a connecting rod 10.

The connection element 4 is pierced at its middle by a vertical bore 11 passing through from one side to the other of said element so as to open within the opening 7 of U shape and between the branches 5, 6.

The central bore 11 comprises from the bottom of the opening 7 of U shape, a first circular portion 12 and a second screw-threaded portion 13 whose internal diameter is greater than that of the first portion. The central bore 11 comprises between two portions 12 and 13 an internal shoulder 14 directed in the direction of the screw-threaded portion 13.

The anchoring screw 3 is constituted by a head 15 with an external profile that is of part spherical shape, prolonged by an elongated and cylindrical body 16 having on its external surface a screw thread 17 for osseous anchoring.

The part spherical head 15 comprises in its internal and central portion an impression 18 of any shape but which is adapted to receive a tool of complementary shape for locking the screw 3 in the osseous portion of the corresponding vertebral body.

The screw-threaded body 16 of the anchoring screw 3 has an external diameter d at the summit of the screw threads 17 which is greater than the external diameter a of the spherical head 15.

This type of screw 3 permits a resistant osseous anchoring because of the large external diameter at the level of the screw thread 17, which is greater than that of its gripping head 15.

On the other hand, and because of the technical constraints of production, of dimensions and resistances to rupture imposed on this type of connector 2, the internal volume d1 of the smooth portion 12 of the central bore 11 is less than the external diameter d of the screw-threaded portion 17 or a of the spherical head 15 of the anchoring screw 3.

Thus, the anchoring screw 3 will receive on the spherical head 15, in the factory or before its osseous anchoring, the connector 2 which is immobilized in a geometrical position by means of a blocking device 19.

The blocking device 19 is provided to adapt itself to the interior and more particularly within the central bore 11 of the connector 2. The blocking device 19 is constituted by a ring 20 and by a screw-threaded and slotted socket 21 adapted to coact with on the one hand with each other about the spherical head 15 of the screw 3 and on the other hand with the portions 12 and 13 of the central bore 11 of the connector 2.

The ring 20 comprises a smooth cylindrical portion 22 bordered at one of its ends by a small collar 23.

The external diameter of the cylindrical portion 22 is slightly less than the internal diameter d1 of the portion 12 of the central bore 11 of the connector 2, whilst the external diameter of the small collar 23 is greater than the internal diameter dl of the portion 12 so that it can come, if necessary, into bearing against the shoulder 14.

The socket 21 is constituted by a cylindrical bore having a screw-threaded external surface 24 and an internally opening bore 25 provided at one of its ends with a diametric reduction forming an internal bearing surface 26 which is a portion of a sphere.

The cylindrical body of the socket 21 comprises on its external surface and in prolongation of the screw-threaded portion 24, an unscrew-threaded shoulder 27.

The socket 21 comprises, in a longitudinal direction, two opposite slots 29, 30 partially cutting the length of the cylindrical body into two separate and identical portions 31, 32.

Opposite the shoulder 27, the socket 21 comprises notches 28 disposed at regular intervals about the periphery of this latter and more particularly at the level and along the axis of the slots 29, 30.

The two separate portions 31, 32 are interconnected at the level of the shoulder 27 by a bridge 33 defining on the one hand a maximum opening before breakage of the slots 29, 30 and on the other hand a maximum elasticity of the socket 21.

Thus, when the slots 29, 30 are in spaced apart position, the internal bore 25 has on the side of the support surface 26 of partial spherical shape, a large inlet opening permitting the passage of the spherical head 15 of the anchoring screw 3.

Thus, the connector 2 is mounted and fixed on the spherical head 15 of the anchoring screw 3 preliminarily blocked in the corresponding vertebral body by means of the blocking device 19.

When the screw 3 is anchored in the vertebral body, the socket 21, in the spaced apart position, is positioned on the spherical head 15. A tool with a claw, not shown, is placed so as to coact with the notches 28 permitting closing the slots 29, 30 and returning against each other the two separate portions 31, 32 of the socket 21 about the spherical head 15.

In this position, the socket 21 is connected in a vertical direction to the spherical head 15, but remains free in rotation and in pivotal angular movement about this latter.

Then, the ring 20 is disposed on the socket 21 such that its small collar 23 penetrates the interior of the bore 25.

The connector 2 is finally screwed on the socket 21 such that its external screw thread 24 coacts with that 13 of the central bore 11 and until the cylindrical portion 22 of the ring 20 coacts with the portion 12 of said bore 11.

The connector 2 is screwed on the socket 21 until this latter comes into abutment against the shoulder 14 of the vertical and internal bore 11 defining the limit of driving in rotation of the connector.

The angular blocking in a predetermined position of the connector 2 about the head 15 of the anchoring screw 3 is effected during immobilization of the connecting rod 10 within the opening 7 of U shape by means of the pressure screw 9.

Thus, during gripping of the pressure screw 9, the clip 8 moves vertically to come into abutment in the upper portion of the branches 5, 6 of the connector 2, whilst the rod 10 comes, under pressure of the screw 9, into bearing against the ring 20 which slides within the socket 21 until it comes to bear against the spherical 15 of the screw 3 driving the securement and blocking of the connector 2.

It should be moreover be understood that the description which precedes is given only by way of example and in no way limits the scope of the invention, which will not be exceeded by replacing the details of embodiment described, by any other equivalents.

The invention claimed is:

1. A vertebral anchoring device, comprising:
a polyaxial anchoring screw having a spherical head opposite a screw-threaded body and configured for being anchored within a vertebral body;
a connecting rod;
a connector configured for receiving the connecting rod and configured for being installed on the spherical head of the anchoring screw, the connector comprising:
a socket having external threads and a ring each being configured to co-act with one other about the spherical head of the screw in an installed orientation in which the ring is disposed on the socket above the spherical head and the socket is connected in a vertical direction to the spherical head but remains free in rotation and in pivotal angular movement about the spherical head, wherein the socket includes two portions bridged together at an upper level of the socket so that the two portions are positionable in a spaced apart orientation to enable the socket to be installed on the spherical head and thereafter the two portions are positionable together about the spherical head to connect the socket to the spherical head and provide the installed orientation;
a connection element comprising a pair of vertical branches delimiting a U-shaped opening for receiving portions of the connecting rod, a threaded central bore located at the bottom of the U-shaped opening and extending through the connection element and being configured to receive the ring and threadably receive the external threads of the socket after the socket has been installed on the spherical head of the screw; and a clip positionable to abut portions of the vertical branches of the connection element and including a pressure screw positionable to engage the connecting rod when the connecting rod is received by the connection element, wherein pressure of the pressure screw against the connecting rod bears the connecting rod against the ring which bears the ring against the spherical head of the screw.

2. The device of claim 1, wherein the central bore comprises the bottom of the U-shaped opening and includes an internal shoulder.

3. The device of claim 1, wherein the screw threaded body has threads having a diameter greater than the diameter of the spherical head.

4. The device of claim 1, wherein the ring comprises a cylindrical portion having a collar.

5. The device of claim 1. wherein the socket includes a spherical bearing surface for engaging the spherical head.

6. The device of claim 1, wherein the socket includes two opposite slots partially cutting the length of the socket into two separate portions.

7. The device of claim 6, wherein the two separate portions are connected by a bridge which allows the separate portions to be positioned relative to one another between a spaced apart position and a together position.

\* \* \* \* \*